United States Patent
Sharpe

(10) Patent No.: US 6,863,659 B2
(45) Date of Patent: Mar. 8, 2005

(54) SHARP SAFE HYDRAULIC RETRACTABLE SYRINGE

(76) Inventor: Bruce George Sharpe, 2 Elfrelda St., Toongabbie, NSW (AU), 2146

( * ) Notice: Subject to any disclaimer, the term of this patent is extended or adjusted under 35 U.S.C. 154(b) by 355 days.

(21) Appl. No.: 10/010,607

(22) Filed: Dec. 10, 2001

(65) Prior Publication Data

US 2003/0109833 A1 Jun. 12, 2003

(51) Int. Cl.⁷ .............................. A61M 5/00; A61M 5/32
(52) U.S. Cl. ........................ 604/110; 604/187; 604/195; 128/919
(58) Field of Search ................................. 604/110, 181, 604/182, 187, 192, 193, 194, 195, 197, 198, 218, 220, 232, 239, 240; 128/919

(56) References Cited

U.S. PATENT DOCUMENTS

| | | | |
|---|---|---|---|
| 3,306,290 A | | 2/1967 | Weltman |
| 4,392,859 A | | 7/1983 | Dent |
| 4,655,751 A | | 4/1987 | Harbaugh |
| 4,664,654 A | | 5/1987 | Strauss |
| 4,801,295 A | | 1/1989 | Spencer |
| 4,816,022 A | | 3/1989 | Poncy |
| 4,840,619 A | | 6/1989 | Hughes |
| 4,955,868 A | | 9/1990 | Klein |
| 4,978,343 A | | 12/1990 | Dysarz et al. |
| 5,046,508 A | * | 9/1991 | Weissler ..................... 600/576 |
| 5,049,133 A | | 9/1991 | Villen Pascual |

* cited by examiner

Primary Examiner—Nicholas D. Lucchesi
Assistant Examiner—Mark K Han

(57) ABSTRACT

Sharp safe hydraulic retractable syringe that is supplied with a hypodermic needle (4) fully housed within an elongated hollow barrel (2) which cannot be used until the plunger rod stop (16) has been removed and the plunger rod (1) has been pushed into the loading position to receive the required liquid into the elongated hollow barrel (2).

The hydraulic retractable syringe assembly is preceded by a retractable mechanism (6-15) that is pre-assembled. The mechanism is contained by a three-legged retaining clip (11) to hold twin conical helical shape springs (14–14d) separated by a spring separation plate (15) within two spring retaining cups (12–13).

Twin conical shape springs are released by the hydraulic pressure exerted by the liquid onto the activating ring with three moulded pistons (8) which passes through a sealing member (9) and exerts axial pressure onto the three release slides (10a, 10b, 10c) to introduce radial pressure onto the three-legged clip (11) to release the conical spring pressure placed onto two spring retaining cups (12–13) causing the twin conical helical shape springs (14–14d) to be set apart and retract up into the elongated hollow barrel. The three-legged retaining clip (11) has two of its three legs preset so as to force the spring separating plate (15) against the hypodermic needle (4) causing the hypodermic needle (4) to misalign and thereby rendering the sharp safe hydraulic retractable syringe non-functional for reuse.

This invention can be incorporated into any syringe.

20 Claims, 8 Drawing Sheets

SHARP SAFE HYDRAULIC RETRACTABLE SYRINGE

BACKGROUND OF THE INVENTION

There are many safety syringe designs available on the market. Most of these designs have as their major purpose the prevention of the spread of infectious diseases and in particular blood borne disease such as AIDS and Hepatitis C, from accidental needle stick to other persons after the needle has been used for a patient with such a disease. The simplest is some form of sheath or shield, which covers the needle either before and/or after use. Typical of these designs are U.S. Pat. No. 4,840,619 Hughes, U.S. Pat. No. 4,816,022 Poncy, U.S. Pat. No. 4,801,295 Spencer, U.S. Pat. No. 4,702,739 Milorad, U.S. Pat. No. 4,664,654 Strauss and U.S. Pat. No. 4,655,751 Harbaugh. These designs are useful in preventing needle stick when disposing of a used syringe but are cumbersome on the syringe, may not be properly deployed, are easy to remove and hence do not prevent improper reuse. It has therefore been proposed to make the needle retract wholly into the syringe body and to be trapped therein. Designs having such a retractable needle are U.S. Pat. No. 3,306,290 Weltman and U.S. Pat. No. 4,392,859 Dent.

These various devices all work well up to a degree but require that the operator manually withdraw the needle back into the barrel by pulling back the plunger rod. The operator may forget to do this, may be distracted before performing this operation, or may not have been instructed to do it. Also manual withdrawal requires that the operator change grip and to use both hands, which is a procedure during which the risk of needle stick to the operator is increased. To overcome these hazards it has been proposed to use spring loaded mechanisms which operate at the end of the injection stroke to push a slideable needle mounting into the barrel and to fully contain the needle therein. Designs that use internal springs to push the needle back into the barrel after use are U.S. Pat. No. 4,978,343 Dysarz et al., U.S. Pat. No. 4,955,868 Klein, and U.S. Pat. No. 5,049,133 Villen Pascual.

However the retraction mechanisms in these designs occupies a significant amount of the internal space of the syringe and hence the fluid volume is consequently significantly reduced. This means that the overall size of the syringe is significantly greater than a standard syringe of the same fluid capacity. Also these designs require full depression of the injection stroke to release the spring mechanism and in some instances the application of increased pressure at the bottom of the stroke to successfully release the spring and initiate retraction of the needle. Further in some of these designs the injection fluid comes into contact with the components of the retraction mechanism resulting in wastage due to fluid remaining in the spaces of the mechanism, and there is also the possibility of contamination of the injection fluid from the materials used in the mechanism.

The need has developed for a retractable type syringe which reliably and automatically withdraws the needle into the syringe body after use, and in which the retraction mechanism is compact such that the overall size of the syringe is not significantly greater than a standard syringe of the same fluid capacity, and in which the injection fluid does not come into contact with the components of the retraction mechanism.

SUMMARY

It is the object of this invention to provide a syringe wherein the hypodermic needle is retracted in to the barrel of the syringe and therefore protects against accidental needle stick after use.

Another object of the present invention is to render the syringe useless after the needle is retracted into the barrel of the syringe and to prevent the accidental reuse of a contaminated syringe as well as preventing intentional reuse by, for example, the users of illicit drugs.

Another object of the present invention is to provide a retractable type syringe that reliably and automatically withdraws the needle into the syringe body after use.

Another object of the present invention is to provide a retractable type syringe in which the retraction mechanism is compact such that the overall size of the syringe is not significantly greater than a standard syringe of the same fluid capacity.

Another object of the present invention is to provide a retractable type syringe in which the injection fluid does not come into contact with the components of the retraction mechanism.

The forgoing and other objects and advantages are attained by a hypodermic syringe with a retracting needle system wherein the retraction mechanism is triggered by the hydraulic pressure within the injection fluid during the injection stoke.

The hypodermic syringe of the present invention comprises a cylindrical body element for containing a fluid; a needle assembly comprising a needle holding member and a hollow needle, the needle holding member repositionable between an injecting position wherein the needle projects axially outward from the body element and a pre-use and post-use position wherein the needle is retracted and contained completely within the body element; a plunger rod reciprocally received into the body element forming a fluid chamber therebetween, and whereby positive and negative pressure forces are generated by adjustment of the plunger rod within the body element whereby fluid is drawn into, and expelled from, the body element through the hollow needle; a retraction mechanism comprising: a spring between the needle holding member and the axial end of the cylindrical body element through which the needle member projects and which generates an axial pressure on the needle holding member; at least one retaining member engaging the needle holding member and retaining the needle holding member against the axial pressure of the spring; at least one activating member within the needle holding member responding to positive fluid pressure within the fluid chamber to release the retaining member from the needle holding member; whereby the needle is automatically deployed into the injecting position by depression of the plunger rod prior to drawing fluid into the fluid chamber and is automatically retracted within the body element at the completion of an injection stroke of the plunger rod and which retraction renders the syringe safe for handling and disposal.

The features of the present invention can best be understood together with further objects and advantages by reference to the following description taken in connection with the accompanying drawings, wherein like numerals indicate like parts.

DETAILED DESCRIPTION OF THE PREFERRED EMBODIMENTS

Figure 1:
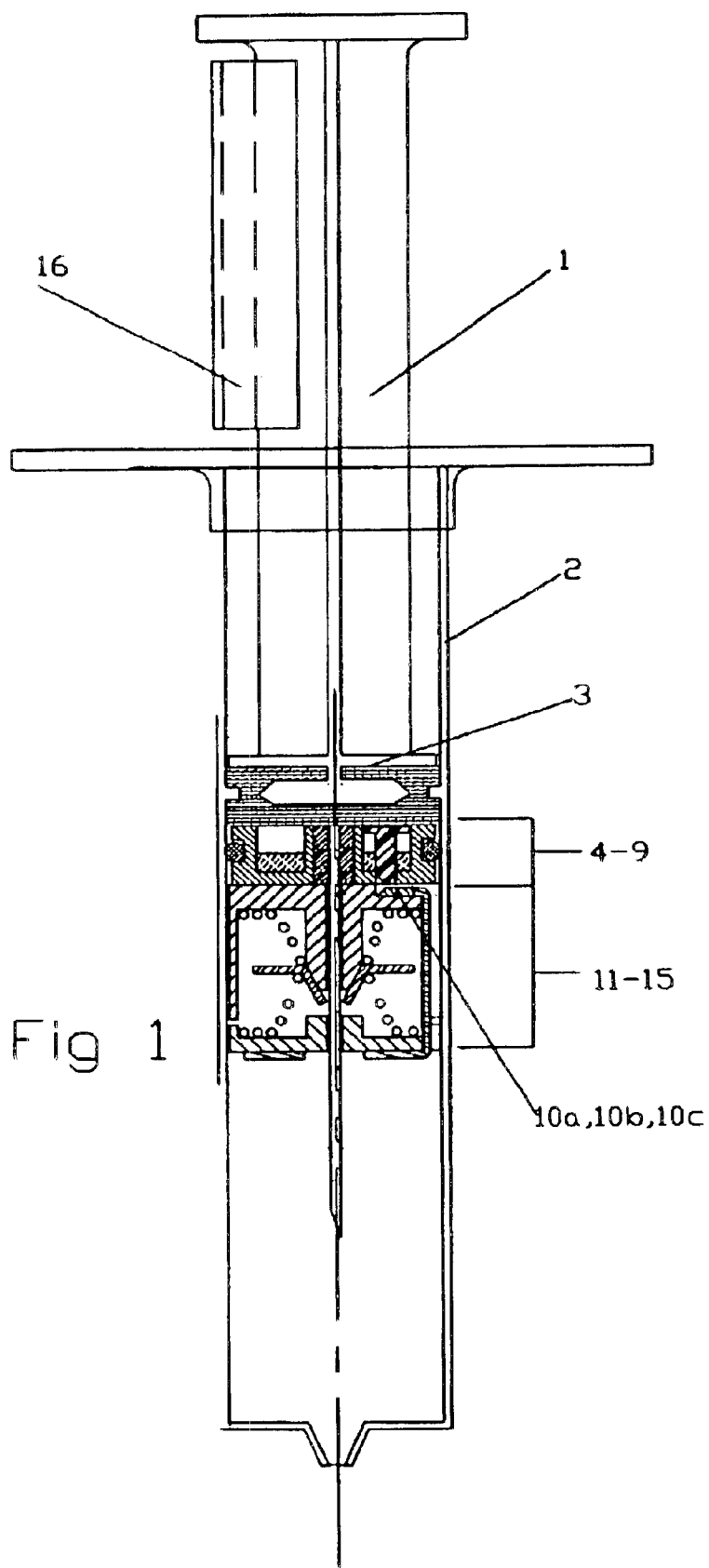
FIG. 1 shows the whole syringe assembly prior to use.
Figure 2:
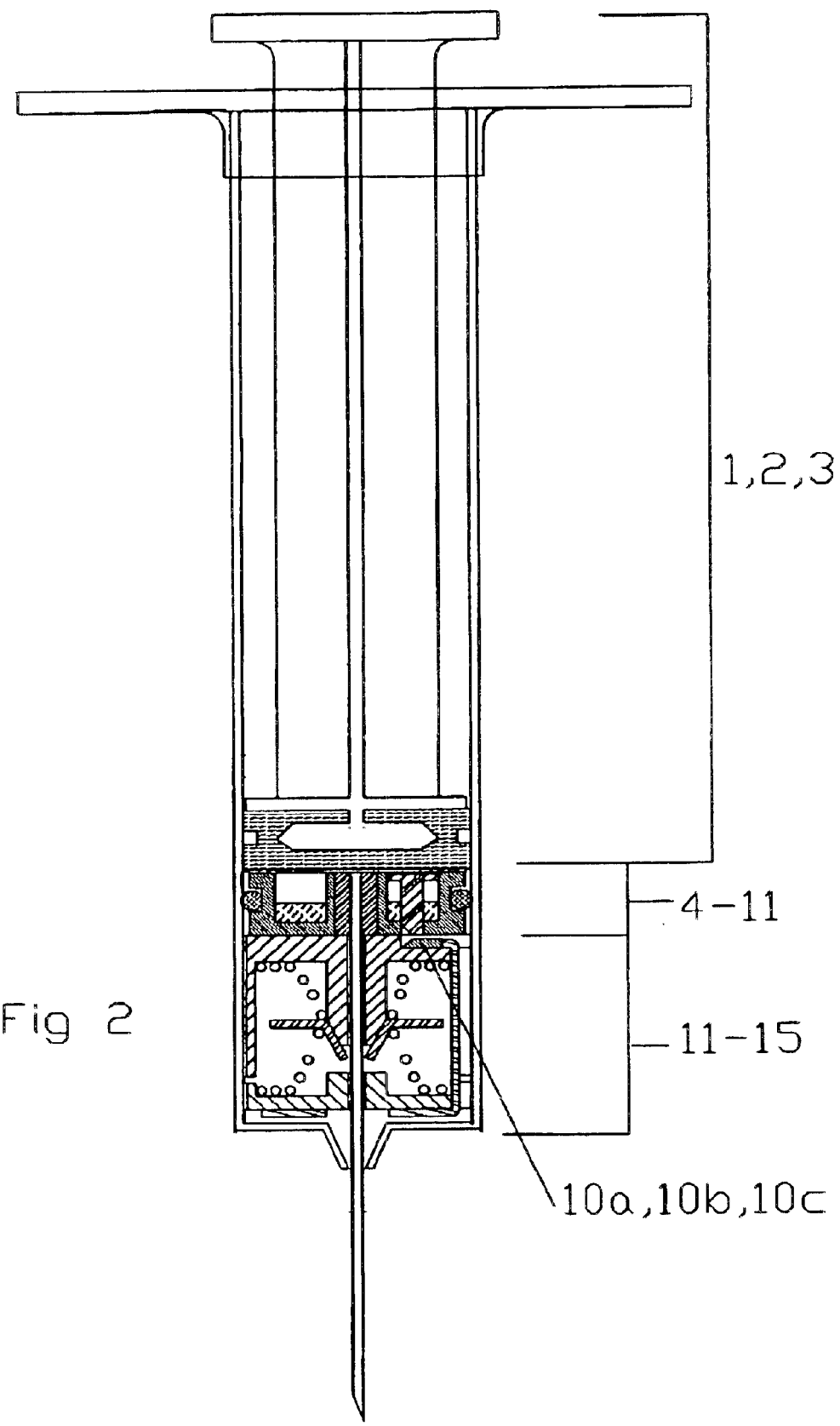
FIG. 2 shows the whole syringe assembly at the end of the needle presentation stroke.
Figure 3:
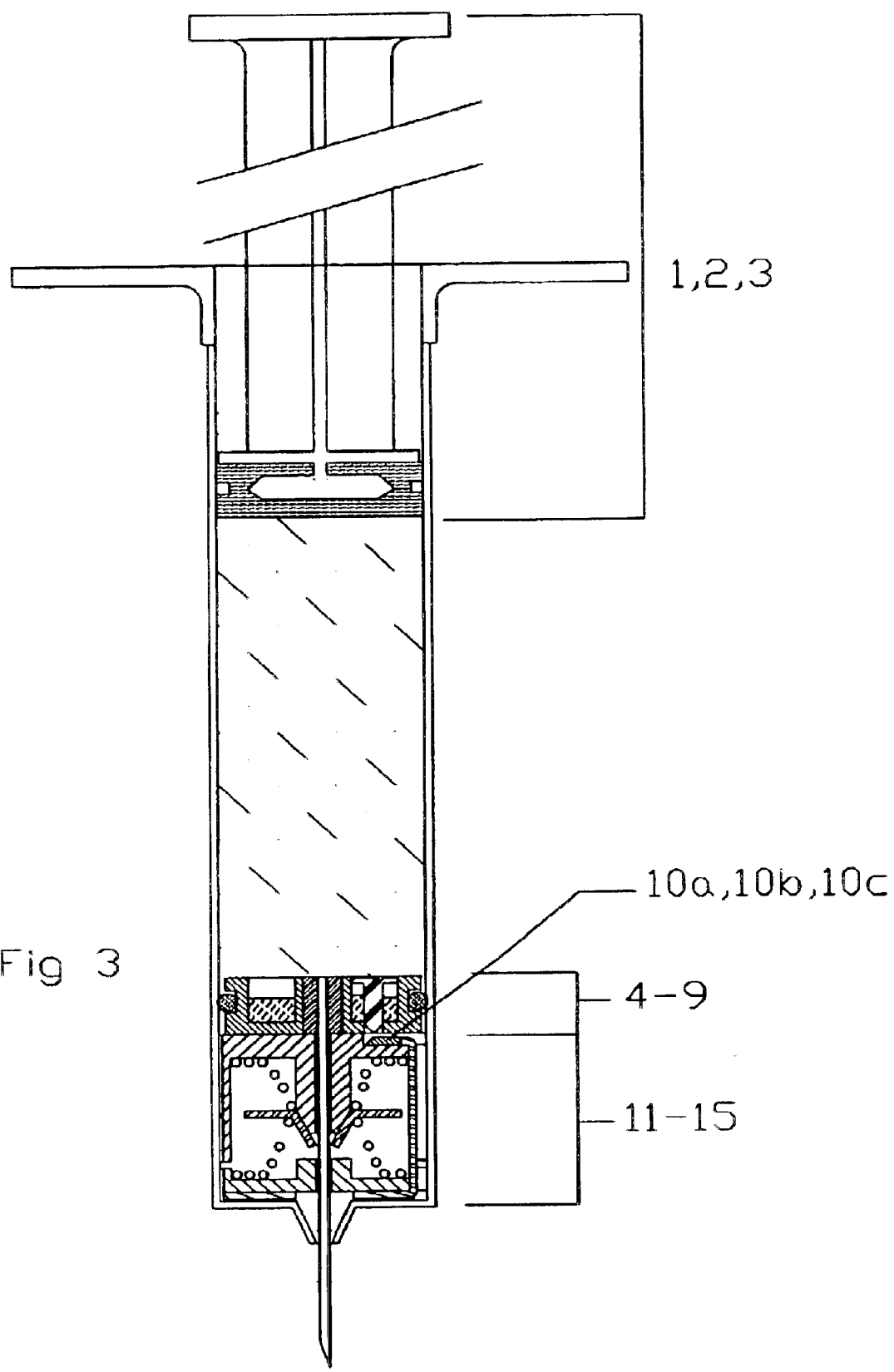
FIG. 3 shows the whole syringe assembly at the end of the injection fluid aspiration stroke.
Figure 4:
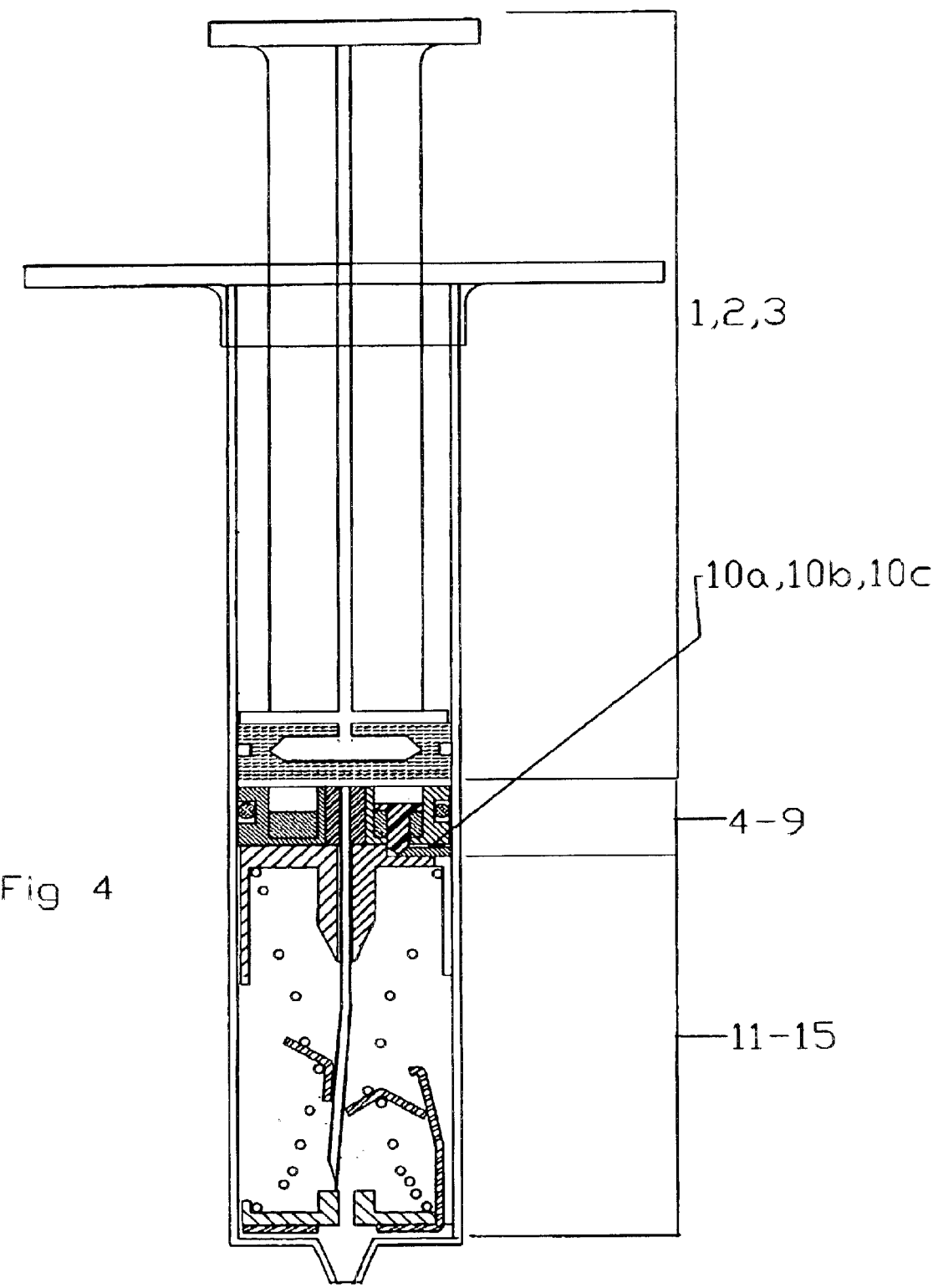
FIG. 4 shows the whole syringe assembly at completion of the injection stroke with the retraction mechanism released and the needle fully retracted within the syringe body.
Figure 5:
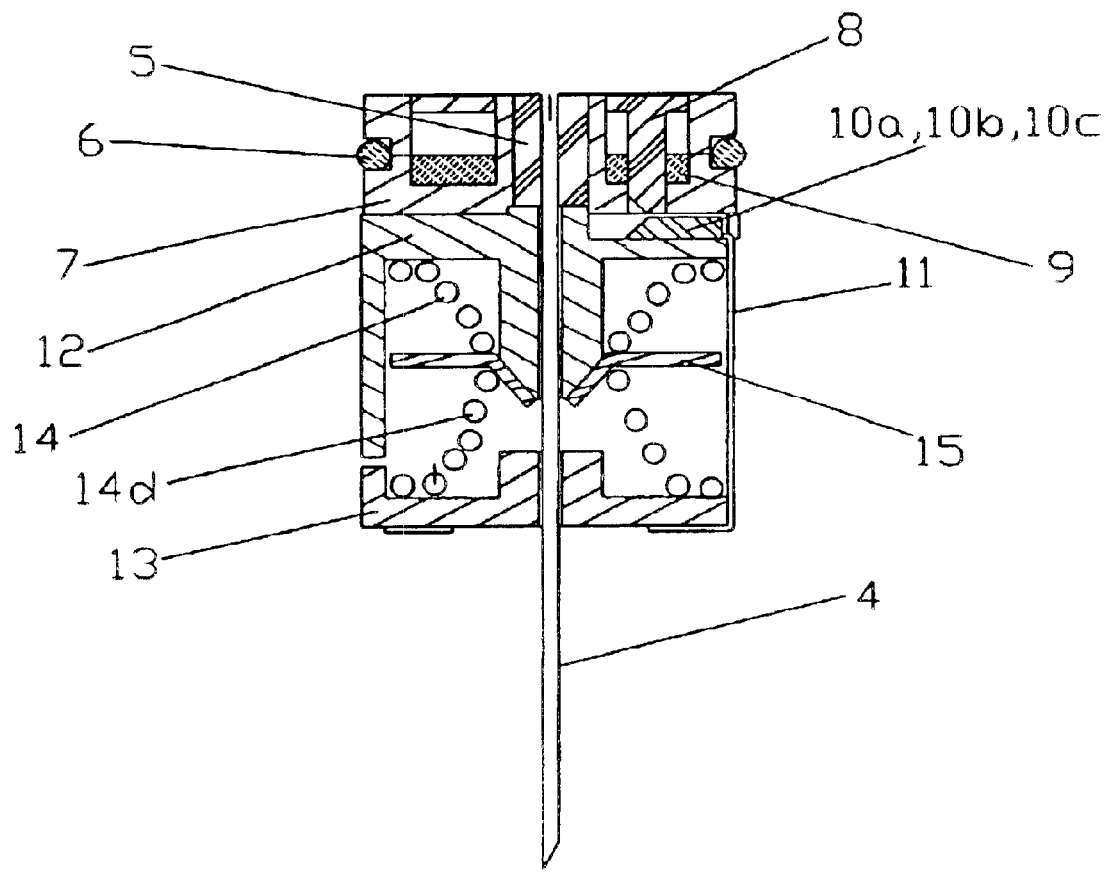
FIG. 5 is a detailed view of the retraction mechanism in the pre-release state.
Figure 6:
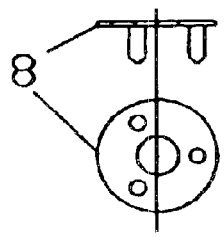
FIGS. 6 to 15 show the individual components of the retraction mechanism.
Figure 7:
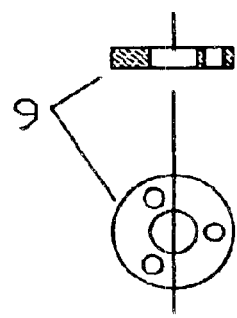
Figure 8:
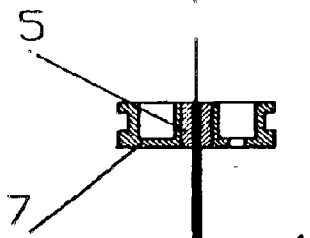
Figure 9:
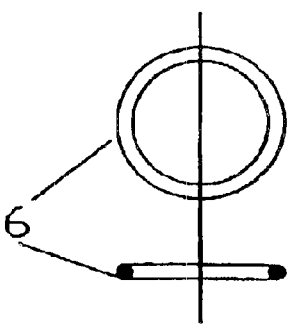
Figure 10:
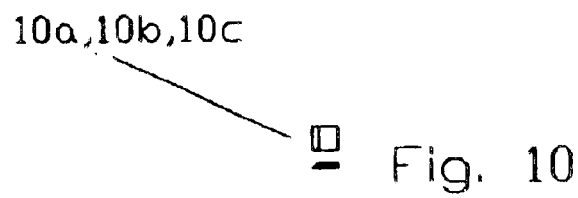
Figure 11:
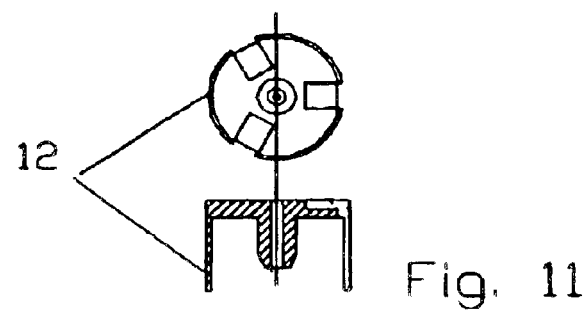
Figure 12:
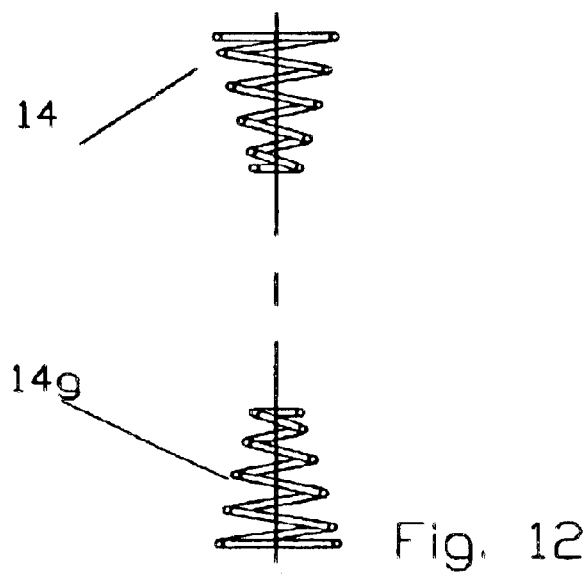
Figure 13:
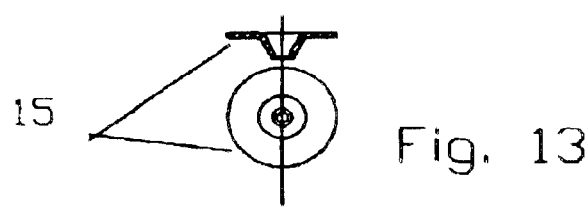
Figure 14:
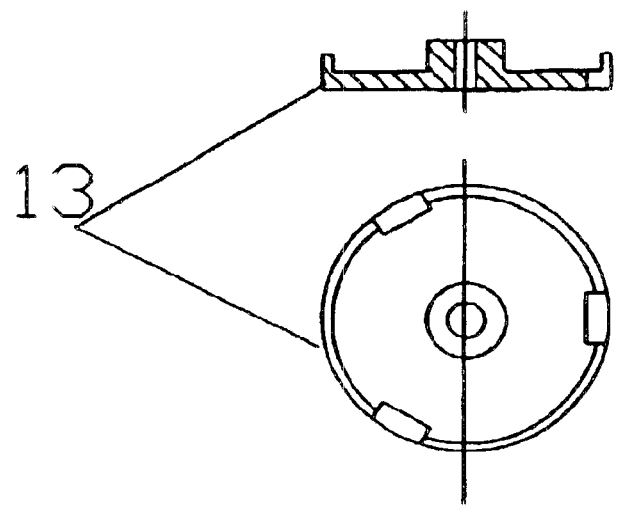
Figure 15:
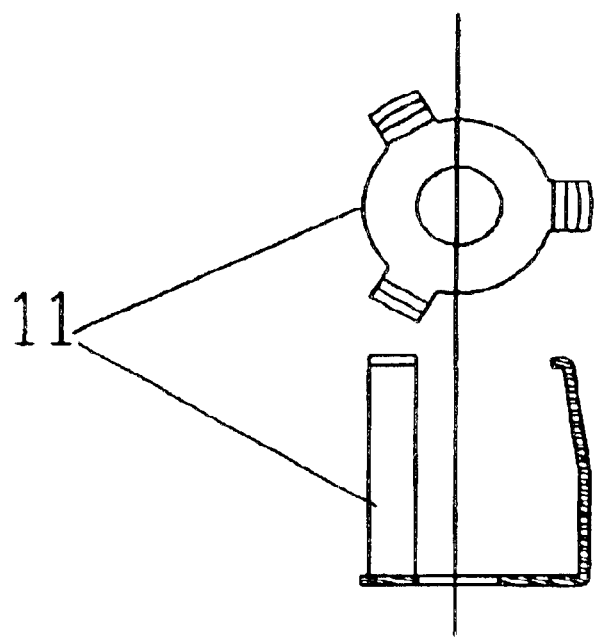

Referring to FIG. 1 there is shown a section elevation view of the syringe of the preferred embodiment.

The syringe is comprised of an elongated hollow barrel 2 with a first end with an opening for a hypodermic needle 4 and a second open end having flanged thumb members. Inside of the elongated hollow barrel 2 is a slideable plunger rod assembly comprising plunger rod 1 with the first end having the sealing member 3 and a second end having a thumb stop in the time honored manner. Removably attached to the plunger rod 1 is a plunger rod stop 16 that prevents the plunger rod assembly moving fully into elongated hollow barrel 2 and hence premature exposure of hypodermic needle 4. Inside the elongated hollow barrel 2 and placed between the first end of the elongated hollow barrel 2 and sealing member 3 is a needle retraction assembly 4-15.

The hypodermic needle 4 is mounted via needle holder member 5 on slideable body 7 that is located within and freely axially displaceable along hollow barrel 2 such that a continuous fluid path exists between the bore of hypodermic needle 4 and the sealing member 6 forming a moveable fluid tight seal between slideable body 7 and the inner wall of hollow barrel 2.

A spring assembly 11-15 is located between slideable body 7 and the first end of hollow barrel 2 and through which hypodermic needle 4 freely passes. Twin conical helical shape springs 14 and 14d are located between 12 and 13. In a preferred form the springs are conical helical shape which has the advantage that when fully compressed the height of the spring is only the thickness of the wire from which it is made. In a more preferred form the springs are twin conical helical shape 14 and 14d twin conical helical shape having a centrally placed spring separating plate 15. Twin conical helical shape springs 14 and 14d are held in compression between the spring retaining cups 12 and 13 by three-legged retaining clip 11 which is located at and cooperating with spring retaining cup 13. Twin conical helical shape springs 14 and 14d are compressed and the three-legged retaining clip 11 fitted to the spring retaining cups 12 and 13 during manufacture so that a user merely has to aspirate and inject in the conventional manner without the need for a spring compression stroke.

Located within the slideable body 7 is the activating ring with three moulded pistons 8 passing through a sealing ring 9. The continuous side of the activating ring with three moulded pistons 8 is exposed to the interior of elongated hollow barrel 2 such that it will be in contact with injection fluid aspirated into the syringe. The other end of the activating ring and three moulded pistons 8 is in contact with the release activating slide 10a, 10b, 10c located in recesses in spring retaining cup 12 and with which the activating ring and three moulded pistons 8 are aligned during assembly. The release activating slide 10a, 10b, 10c each engage catch ends of respective legs of three-legged retaining clip 11, which catch ends are also located in the same respective recesses in spring retaining cup 12 as respective to the release activating slide 10a, 10b, 10c.

The operation cycle of the sharp safe hydraulic retractable syringe is that the user removes plunger rod stop 16 and fully depresses the plunger rod 1 assembly to fully deploy the hypodermic needle 4 through the opening in the first end of elongated hollow barrel 2. The user then aspirates injection fluid into the 'syringe' and performs an injection in the conventional manner. During the injection stroke the hydraulic pressure of the injection fluid is raised forcing the activating ring with three moulded pistons 8 against the release activating slide 10a, 10b, 10c which convert the axial pressure of the activating ring with three moulded pistons 8 to a radial pressure acting on the catch ends of respective legs. This radial pressure displaces the catch ends of three-legged retaining clip 11 from the recesses of the release activating slide 10a, 10b, 10c into the grooves on the outside of spring retaining cup 12 thus allowing the springs to expand when the hydraulic pressure falls at the completion of the injection stroke. Thus the springs force the slideable body 7 on which hypodermic needle 4 is mounted away from the first end of, and fully into, elongated hollow barrel 2. Three-legged retaining clip 11 has two of its three legs preset so as to force the Spring separating plate 15 against hypodermic needle 4 causing it to be axially misaligned and incapable of re-emerging through the opening in the first end of elongated hollow barrel 2.

Although the system described in detail above has been found to be most satisfactory and preferred, many variations are possible. Although the invention has been described with reference to the preferred embodiment, it will be understood by those skilled in the art that additions, modifications, substitutions, deletions and other changes not specifically described, may be made to the embodiments herein, it should be understood that the details herein are to be interpreted as illustrative and are not in a limiting sense.

What is claimed as the invention is:

1. A single use hypodermic syringe with a retracting needle system comprising:
   a cylindrical body element for containing a fluid;
   a needle assembly comprising a needle holding member and a hollow needle, the needle holding member repositionable between an injecting position wherein the needle projects axially outward from the body element and a pre-use and post-use position wherein the needle is retracted and contained completely within the body element;
   a plunger rod reciprocally received into the body element forming a fluid chamber between the cylindrical body element, the plunger and the needle holding member, and whereby positive and negative pressure forces are generated by adjustment of the plunger within the body element whereby fluid is drawn into, and expelled from, the body element through the hollow needle;
   a retraction mechanism comprising:
   a spring between the needle holding member and the axial end of the cylindrical body element through which the needle member projects and which generates an axial pressure on the needle holding member;
   at least one retaining member engaging the needle holding member and retaining the needle holding member against the axial force of the spring;
   at least one activating member within the needle holding member responding to positive fluid pressure within the fluid chamber to release the retaining member from the needle holding member;
   whereby the needle is automatically deployed into the injecting position by depression of the plunger prior to drawing fluid into the fluid chamber and is automatically retracted within the body element at the completion of an injection stroke of the plunger and which retraction renders the syringe safe for handling and disposal.

2. The hypodermic syringe of claim 1 wherein said activating member comprises an activating ring with pistons attached cooperating with an activating release slide, whereby positive fluid pressure within the fluid chamber pushes the activating ring piston against the activating release slide which in turn releases the retaining clip from the needle holding member.

3. The hypodermic syringe of claim 1 wherein the spring is conical helical spring.

4. The hypodermic syringe of claim 3 wherein the spring is a twin conical helical spring.

5. The hypodermic syringe of claim 4 wherein the twin conical helical spring includes a spring separation member.

6. The hypodermic syringe of claim 1 wherein the spring are received between a pair of spring retaining cups.

7. The hypodermic syringe of claim 6 wherein one of spring retaining cups is integrally formed with the needle holding member.

8. The hypodermic syringe of claim 1 wherein a plurality of activation members are equidistantly spaced around the needle holding member, each activation member cooperating with a corresponding retaining member.

9. The hypodermic syringe of claim 8 wherein a slide member is located between each activation member and each corresponding retaining member.

10. The hypodermic syringe of claim 5 wherein the twin conical spring and the spring separation member cooperate to deflect the hollow needle from axial alignment when in the post-use position.

11. A single use hypodermic syringe with a retracting needle system comprising:
a cylindrical body element for containing a fluid;
a needle assembly comprising a needle holding member and a hollow needle, the needle holding member repositionable between an injecting position wherein the needle projects axially outward from the body element and a pre-use and post-use position wherein the needle is retracted and contained completely within the body element;
a plunger reciprocally received into the cylindrical body element forming a fluid chamber between the cylindrical body element and the needle holding member, and whereby positive and negative pressure forces are generated by adjustment of the plunger within the body element whereby fluid is drawn into, and expelled from, the cylindrical body element through the hollow needle;
a retraction mechanism comprising:
a spring between the needle holding member and the axial end of the cylindrical body element through which the needle member projects and which generates an axial force on the needle holding member, wherein the spring is a twin conical helical springs and include a spring separation member and is received between a pair of spring retaining cups, both spring retaining cups being integrally formed with the needle holding member;
at least one retaining member engaging the needle holding member and retaining the needle holding member against the axial force of the spring;
a plurality of activating members within the needle holding member equidistantly spaced around the needle holding member moulded on a ring, responding to positive fluid pressure within the fluid chamber to release a corresponding retaining member from the needle holding member, and a slide member located between each activation member and each corresponding retaining member;
whereby the needle is automatically deployed into the injecting position by depression of the plunger prior to drawing fluid into the fluid chamber and is automatically retracted within the cylindrical body element at the completion of an injection stroke of the plunger and which retraction renders the syringe safe for handling and disposal.

12. A needle retraction mechanism for a single use hypodermic syringe having a cylindrical body element for containing a fluid and a plunger reciprocally received into the body element forming a fluid chamber between the cylindrical body element and the needle holding member, and whereby positive and negative pressure forces are generated by adjustment of the plunger within the cylindrical body element whereby fluid is drawn into, and expelled from, the cylindrical body element through the hollow needle, comprising:
a needle assembly comprising a needle holding member and a hollow needle, the needle holding member repositionable between an injecting position wherein the needle projects axially outward from the body element and post-use position wherein the needle is retracted and contained completely within the cylindrical body element;
a spring between the needle holding member and the axial end of the cylindrical body element through which the needle member projects and which generates an axial force on the needle holding member;
at least one retaining member engaging the needle holding member and retaining the needle holding member against the axial force of the spring;
at least one activating member within the needle holding member responding to positive fluid pressure within the fluid chamber to release the retaining member from the needle holding member comprising:
an activating ring piston cooperating with an activating release slide, whereby positive fluid pressure within the fluid chamber pushes the activating ring piston against the activating release slide which in turn releases the retaining clip from the needle holding member.

13. The needle retraction mechanism of claim 12 wherein the spring is a conical helical spring.

14. The needle retraction mechanism of claim 13 wherein the spring is a conical helical spring.

15. The needle retraction mechanism of claim 14 wherein the twin conical helical spring includes a spring separation member.

16. The needle retraction mechanism of claim 12 wherein the spring is received between a pair of spring retaining cups.

17. The needle retraction mechanism of claim 16 wherein both spring retaining cups are integrally formed with the needle holding member.

18. The retraction mechanism of claim 12 wherein a plurality of activation members are equidistantly spaced around the needle holding member moulded on a ring, the activation member cooperating with a corresponding retaining member.

19. The needle retraction mechanism of claim 18 wherein a slide member is located between each activation member and each corresponding retaining member.

20. A needle retraction mechanism of claim 15 wherein the twin conical spring and the spring separation member cooperate to deflect the hollow needle from axial alignment when in the post-use position.

* * * * *